(12) United States Patent
Lee et al.

(10) Patent No.: US 10,327,700 B2
(45) Date of Patent: Jun. 25, 2019

(54) INTELLIGENT INSOLE

(71) Applicant: NATIONAL TSING HUA UNIVERSITY, Hsinchu (TW)

(72) Inventors: Yu-Chi Lee, Hsinchu (TW); Mao-Jiun Wang, Hsinchu (TW); Chun Zhang, Marietta, GA (US); Hsu-Pin Wang, Atlanta, GA (US)

(73) Assignee: National Tsing Hua University, Hsinchu (TW)

( * ) Notice: Subject to any disclaimer, the term of this patent is extended or adjusted under 35 U.S.C. 154(b) by 384 days.

(21) Appl. No.: 15/196,947

(22) Filed: Jun. 29, 2016

(65) Prior Publication Data

US 2017/0238870 A1 Aug. 24, 2017

(30) Foreign Application Priority Data

Feb. 24, 2016 (TW) .............................. 105105379 A

(51) Int. Cl.
| | |
|---|---|
| A43B 3/00 | (2006.01) |
| A61B 5/00 | (2006.01) |
| A43B 17/00 | (2006.01) |
| A43B 17/14 | (2006.01) |
| A61B 5/103 | (2006.01) |
| A61B 5/107 | (2006.01) |
| B33Y 80/00 | (2015.01) |

(52) U.S. Cl.
CPC .......... *A61B 5/6807* (2013.01); *A43B 3/0005* (2013.01); *A43B 17/14* (2013.01); *A61B 5/1038* (2013.01); *A43B 17/00* (2013.01); *A61B 5/1074* (2013.01); *A61B 5/486* (2013.01); *A61B 5/746* (2013.01); *A61B 2562/029* (2013.01); *A61B 2562/0247* (2013.01); *A61B 2562/0271* (2013.01); *A61B 2562/066* (2013.01); *B33Y 80/00* (2014.12)

(58) Field of Classification Search
None
See application file for complete search history.

(56) References Cited

U.S. PATENT DOCUMENTS 5,929,332 A * 7/1999 Brown ..................... A43B 3/00
36/136
6,026,599 A * 2/2000 Blackwell ............ A43B 1/0027
36/140

(Continued)

*Primary Examiner* — Sean P Dougherty
(74) *Attorney, Agent, or Firm* — Muncy, Geissler, Olds & Lowe, P.C.

(57) ABSTRACT

An intelligent insole is provided. The intelligent insole includes an insole body, a pressure sensor, a temperature sensor, a humidity sensor and a signal collector. The pressure sensor, the temperature sensor and the humidity sensor are formed on the surface of the insole body, and the above sensors and the insole body are manufactured via the same 3D printing process. The pressure sensor senses the pressure signal from the insole body in contact with the foot. The temperature sensor and the humidity sensor respectively sense the temperature signal and the humidity signal of the insole body. The signal collector is respectively electrically connected to the pressure sensor, the temperature sensor and the humidity sensor to receive the pressure signal, the temperature signal and the humidity signal and then transmit the signals to a signal receiver via wireless transmission.

9 Claims, 4 Drawing Sheets

(56) References Cited

U.S. PATENT DOCUMENTS

| | | | | |
|---|---|---|---|---|
| 6,131,311 | A * | 10/2000 | Brown | A43B 7/142 |
| | | | | 36/145 |
| 7,426,873 | B1 * | 9/2008 | Kholwadwala | A43B 3/00 |
| | | | | 73/777 |
| 8,389,862 | B2 * | 3/2013 | Arora | H01L 23/4985 |
| | | | | 174/254 |
| 9,453,772 | B2 * | 9/2016 | Ross | A43B 3/0005 |
| 9,886,834 | B2 * | 2/2018 | Hyde | G08B 21/0469 |
| 2003/0009308 | A1 * | 1/2003 | Kirtley | A61B 5/1038 |
| | | | | 702/141 |
| 2003/0163287 | A1 * | 8/2003 | Vock | A43B 3/0005 |
| | | | | 702/187 |
| 2010/0324455 | A1 * | 12/2010 | Rangel | A43B 7/147 |
| | | | | 600/592 |
| 2012/0109013 | A1 * | 5/2012 | Everett | A61B 5/1036 |
| | | | | 600/587 |
| 2012/0234111 | A1 * | 9/2012 | Molyneux | A43B 3/00 |
| | | | | 73/862.541 |
| 2013/0192071 | A1 * | 8/2013 | Esposito | A61B 5/1036 |
| | | | | 33/6 |
| 2013/0204157 | A1 * | 8/2013 | Clark | A61F 2/4657 |
| | | | | 600/547 |
| 2014/0182170 | A1 * | 7/2014 | Wawrousek | A43B 7/14 |
| | | | | 36/103 |
| 2014/0200486 | A1 * | 7/2014 | Bechtel | A61B 5/14551 |
| | | | | 600/592 |
| 2015/0217163 | A1 * | 8/2015 | Amis | A61B 5/0022 |
| | | | | 700/91 |
| 2015/0260514 | A1 * | 9/2015 | Menelas | A43B 3/0005 |
| | | | | 702/2 |
| 2015/0309563 | A1 * | 10/2015 | Connor | G06F 3/011 |
| | | | | 73/865.4 |
| 2017/0173885 | A1 * | 6/2017 | Kaur | A43B 17/00 |
| 2018/0256071 | A1 * | 9/2018 | Mathieu | A43B 3/0005 |

* cited by examiner

INTELLIGENT INSOLE

CROSS-REFERENCE TO RELATED APPLICATION

This application claims priority from Taiwan Patent Application No. 105105379, filed on Feb. 24, 2016, in the Taiwan Intellectual Property Office, the content of which is hereby incorporated by reference in its entirety for all purposes.

BACKGROUND OF THE INVENTION

1. Field of the Invention

The present invention relates to an intelligent insole with the sensor. More particularly, the present invention relates to an intelligent insole having the pressure sensors, temperature sensors and humidity sensors capable of presenting the pressure, temperature and humidity status of the feet, so as to provide the healthcare advice.

2. Description of the Related Art

Nowadays, everyone wears shoes during most part of the day on daily basis. There are shoes for all kinds of activities, whether to travel, work or sports, which mainly serve as a form of feet protection as well as decorative purpose. For instance, there will be shoes with functions specifically for carrying out different activities such as walking, jogging, hiking, etc., such that the feet can get suitable assistance and protection during the activity. Meanwhile the feet condition, especially the soles of the feet can represent the health of the person, so choosing the right shoes is vital for quality of everyday life.

Nevertheless, for majority of the shoes, the feet will be sealed inside, on top of the bad ventilation, the sweat from the feet during activities such as walking or sports will cause the humidity therein to rise. Bacteria and molds tend to grow under the warm and humid condition, affecting the foot health. Moreover, everybody has different soles in terms of shape, so not everyone's feet can fit into the same model of shoes. A person might suffer from problems like foot deformation or uneven tension on the foot if such person has worn a pair of poor fitting shoes for a long time. Henceforth, most people will replace the insole of his/her shoes, for example the insoles with special material or design to tackle the aforementioned problems.

Alas, a pair of ordinary insoles can only provide solutions to some of the problems, as most people would not pay attention to the rise in temperature and humidity inside the shoes after prolonged period of wearing, as well as the pressure distribution of the feet. So, in most of the cases it will be too late to rectify the problems once the repercussion has emerged, since the damage has already been done to the feet. As a result, the inventor of the present invention designs an intelligent insole in order to solve the problems by eliminating the drawbacks in the present art, thereby improving the application in related fields.

SUMMARY OF THE INVENTION

In light of the aforementioned technical issues, the objective of the present invention is to provide an intelligent insole with pressure, temperature and humidity sensors, so as to solve the problems, i.e. ordinary insole cannot detect the pressure, temperature and humidity of the feet simultaneously.

In accordance to the objective of the present invention, an intelligent insole is provided. The intelligent insole includes an insole body, a pressure sensor, a temperature sensor, a humidity sensor and a signal collector. The insole body is formed via 3D printing. The pressure sensor is formed on the surface of the insole body via 3D printing to sense the pressure signal from the insole body in contact with the foot. The temperature sensor is formed on the surface of the insole body via 3D printing for sensing the temperature signal of the insole body. The humidity sensor is formed on the surface of the insole body via 3D printing to sense the humidity signal of the insole body. Wherein, the pressure sensor, the temperature sensor, the humidity sensor and the insole body are formed in the same 3D printing process. The signal collector is respectively electrically connected to the pressure sensor, the temperature sensor and the humidity sensor to receive the pressure signal, the temperature signal and the humidity signal and then transmit the signals to a signal receiver via wireless transmission.

Preferably, the pressure sensor is disposed in a region where the insole body and the foot come into contact; the pressure sensor measures the variation of electric potential caused by the foot exerting force on the insole body to obtain the pressure signal.

Preferably, the temperature sensor and the humidity sensor are disposed in a region where the insole body and the foot do not come into contact to sense the temperature and humidity status of the insole and obtain the temperature signal and the humidity signal.

Preferably, the pressure sensor, the temperature sensor and the humidity sensor are respectively approximately 0.001 to 0.003 mm in thickness.

Preferably, the areas of the pressure sensor, the temperature sensor and the humidity sensor are respectively approximately 2 to 8 mm$^2$.

Preferably, the materials for the pressure sensor, the temperature sensor and the humidity sensor include electrically conducting metal or piezoelectric material.

Preferably, the signal receiver is a handheld mobile device displaying sensor readings of the pressure signal, the temperature signal and the humidity signal on a display panel thereof.

Preferably, the handheld mobile device includes a health management application including a plurality of critical values corresponding to the pressure signal, the temperature signal and the humidity signal. The health management application sends out a warning when sensed signals exceed the corresponding critical values.

Preferably, the health management application may connect to a cloud server, uploads the pressure signal, the temperature signal and the humidity signal in a predetermined time for storage in the cloud server.

Preferably, the cloud server includes a diagnosis advice corresponding to the pressure signal, the temperature signal and the humidity signal; the diagnosis advice is transmitted back to the handheld mobile device and displayed on the display panel thereof to provide healthcare advices.

In conclusion, the intelligent insole of the present invention may have one or more advantage listed as follows:

(1) The insole body and the pressure sensor, temperature sensor and the humidity sensor on the surface of the intelligent insole could be simultaneously formed in the same 3D printing process, thereby reducing the number of steps required to manufacture the insole while improving the product quality.

(2) The pressure sensor, temperature sensor and the humidity sensor on the intelligent insole are micro-sensors with thickness less than known sensors in the art, such that no uncomfortable lumpy sensation will be caused to the feet even if the sensors are formed on the surface of the insole body, and the comfortability of the shoes is improved. In addition, the present invention avoids the disposing of protruding sensors, which reduces the durability of the insole due to constant abrasion while being worn.

(3) The intelligent insole of the present invention is capable of transmitting the sensed pressure signal, temperature signal, and the humidity signal to the signal receiver to compare with the critical values such that a warning is delivered if anomaly is detected. The present invention may even upload the sensed data to the cloud server to compare with the standard models stored therein in order to find the corresponding diagnosis advice, so the user is able to receive proper healthcare advice, thereby improving the practicability of the intelligent insole.

DESCRIPTION OF THE PREFERRED EMBODIMENTS

The present invention has been described with some preferred embodiments thereof and it is understood that many changes and modifications in the described embodiments can be carried out without departing from the scope and the spirit of the invention that is intended to be limited only by the appended claims.

Figure 1A:
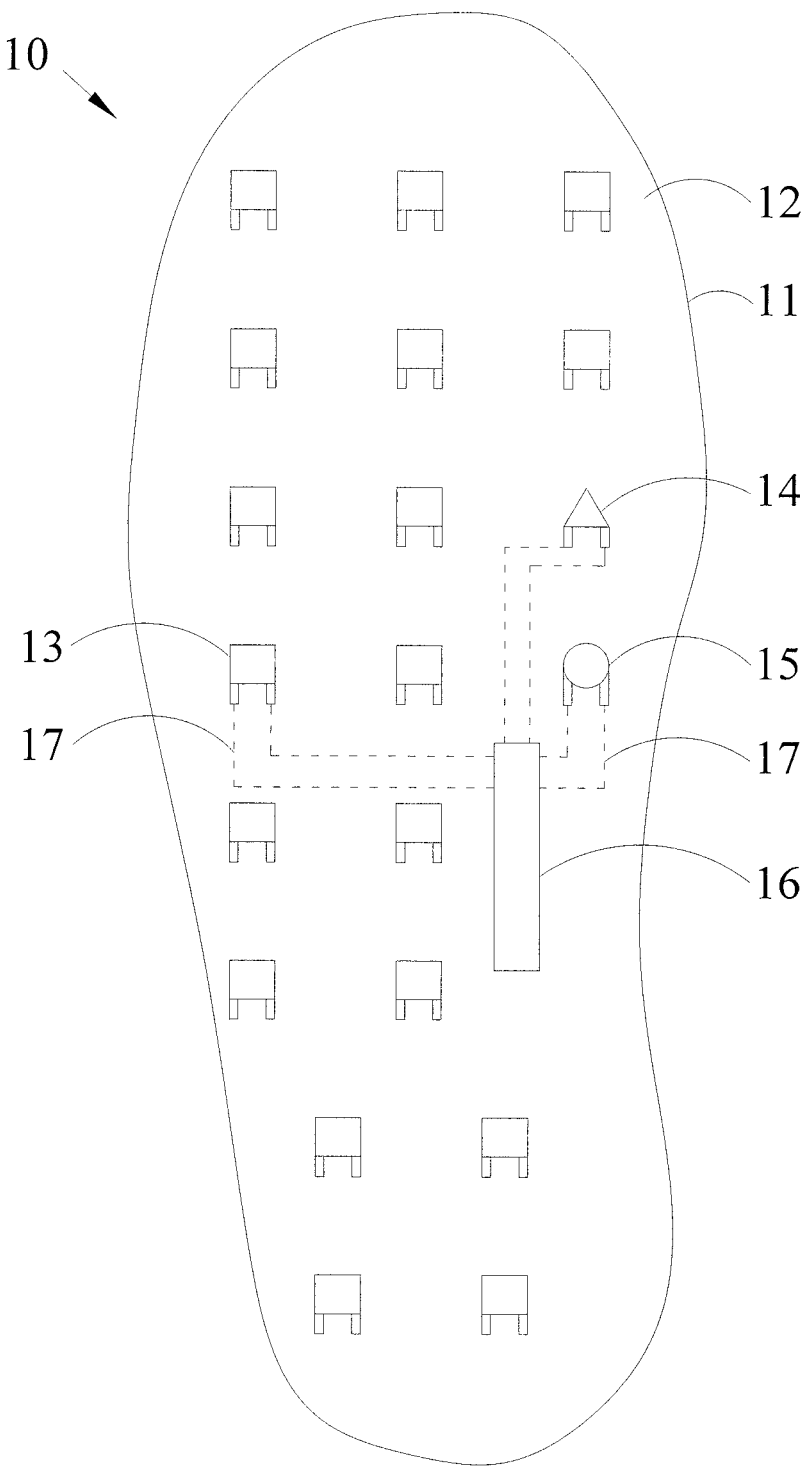
FIGS. 1A and 1B are the schematic diagrams illustrating the embodiments of the intelligent insole of the present invention.

Referring to the FIG. 1A, which is the schematic diagram illustrating the intelligent insole of the present invention. As shown in the figure, the intelligent insole 10 of the present invention may include insole body 11 which may contain materials such as ethylene-vinyl acetate (EVA), polyurethane (PU), etc. For the initial step to manufacture the insole body 11, the design drawing containing the exterior shape information such as the dimensions of the insole body 11, including the length, width, thickness, etc. thereof is fed into the 3D printer. Then the materials for the insole are selected and the 3D printer will print the insole body 11. Since everybody has different size and shape of feet, so the 3D printing technique is applied such that the customized insoles matching the feet of different users can be manufactured rapidly, by adjusting the dimensions of the design drawing. The present invention may even integrate with a 3D scanner which scans the feet of the users directly and then transforms the scanner data into a design drawing applicable to the 3D printer to further save the time spent on measuring and drafting.

Then, a plurality of sensors could be disposed on the surface 12 of the insole body 11, including the pressure sensor 13, the temperature sensor 14, and the humidity sensor 15. The aforementioned sensors contain the sensing circuits of the pressure, temperature and humidity, which could be printed on the surface 12 of the insole body 11 via 3D printing in a similar fashion. When the foot and the insole body 11 come into contact, the pressure sensor 13 may sense the pressure status by measuring a variation of electric potential, i.e. the magnitude of the potential difference in the sensing circuits, such that a pressure signal is obtained. On the other hand, the temperature sensor 14 and the humidity sensor 15 could be respectively disposed with resistors having temperature coefficient and humidity coefficient, thereby sensing the variation of temperature and humidity by measuring the variation of resistance such that the temperature and humidity signals are obtained. The materials for the sensing circuits may include electrically conducting metal or piezoelectric material. Since the sensing circuits are formed on the surface 12 via 3D printing, the pressure sensor 13, temperature sensor 14, humidity sensor 15 and the insole body 11 could be finished in the same 3D printing process during the manufacturing of the intelligent insole 10, thus minimizing the number of manufacturing steps required while improving the product quality, e.g. the adhesive strength of the sensors to the insole. In the meantime, the pressure sensor 13, the temperature sensor 14 and the humidity sensor 15 are microelectronic circuits with thickness ranging from approximately 0.001-0.003 mm, while the area of each sensor is approximately 2-8 $mm^2$. For instance, in a preferred embodiment, every sensor could be 1 mm×3 mm×0.002 mm in length, width and thickness respectively. Since the sensors in the present invention are significantly thinner than the conventional sensors, so no uncomfortable lumpy sensation will be caused to the feet even if the sensors are formed on the surface 12 of the insole body 11 and there is no need to dispose the notches in the insole body 11 to accommodate the sensors. Hence, the present invention is superior to the conventional insoles with sensors in terms of comfort and durability.

Moreover, the pressure sensor 13, the temperature sensor 14 and the humidity sensor 15 could be electrically connected to the signal collector 16 through the wiring 17. The signal collector 16 may collect the pressure signal, the temperature signal, and the humidity signals respectively from the pressure sensor 13, temperature sensor 14 and the humidity sensor 15, and then transmit the signals to a signal receiver via wireless telecommunications such as Bluetooth, WiFi, RFID, etc. Only part of the wiring 17 connected to the pressure sensor 13, the temperature sensor 14 and the humidity sensor 15 is shown in the FIG. 1A, whereas other sensors could be connected to the signal collector 16 via similar wiring 17. The wiring 17 could be simultaneously formed on the surface 12 of the insole body 11 via the 3D printing. Since the wiring 17 and the sensors may have similar thickness and material, the wiring 17 formed on the surface 12 will not cause discomfort to the feet.

As can be further appreciated in the FIG. 1A, the pressure sensors 13 are disposed around the region where the foot comes into direct contact with the insole body 11, i.e. around the regions of the toes, forefoot, midfoot, and the heel. In which, every sensor could be set apart from each other by a separation distance of approximately 5-15 mm. The number of pressure sensors 13 disposed in the insole body 11 is typically around 15-25, which could be adjusted according to the size of the foot. The temperature sensor 14 and the humidity sensor 15 are disposed around the arch of the foot, i.e. the region where the foot does not come into direct contact with the insole body 11, in order to detect the temperature and humidity status inside the shoe. The number of temperature sensor 14 and humidity sensor 15 disposed in the insole body 11 are not limited to 1 as shown in the FIG. 1A. A plurality of temperature sensors 14 and humidity sensors 15 could be disposed in the insole body 11 in a way similar to the pressure sensors 13, i.e. separated from each other by a fixed separation distance.

Figure 1B:
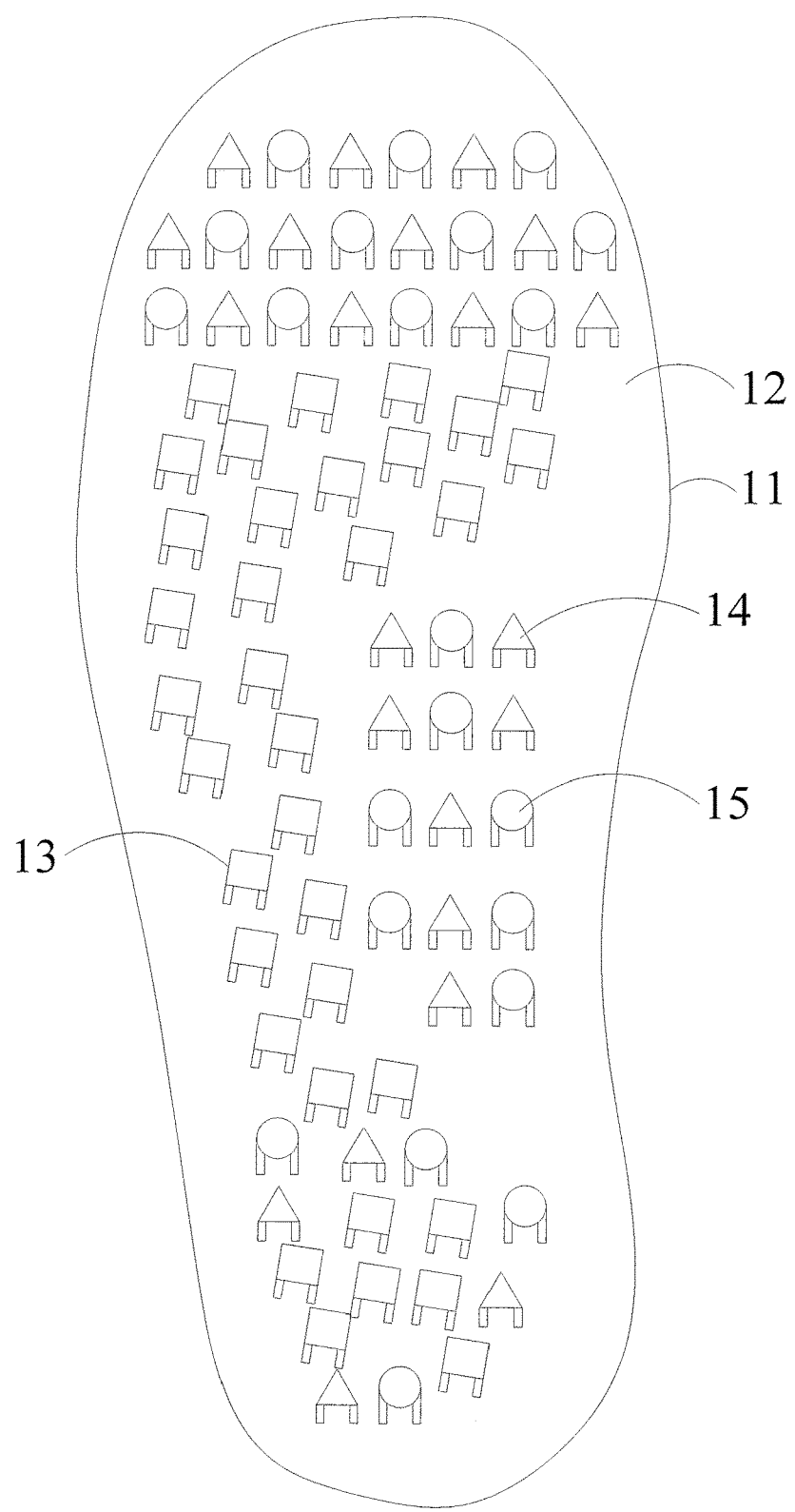

Besides, the distribution of the pressure sensor 13, temperature sensor 14 and the humidity sensor 15 are not limited to the pattern shown in FIG. 1A. For instance, the temperature sensor 14 or the humidity sensor 15 could be disposed around the forefoot and the heel to detect the temperature and humidity of the region where the foot comes into contact with the insole body 11. Refer to FIG. 1B, which illustrates another embodiment of the intelligent insole of the present invention. As shown in the figure, for the practical distribution pattern of the sensors on the insole body 11 the majority of the temperature sensors 14 and the humidity sensors 15 could be distributed in the regions around the toes and the arch of the foot while the minority thereof could be distributed in the region around the heel, whereas the pressure sensors 13 could be scattered around the surface 12 of the insole body 11, mainly the regions around the toes, metatarsus, lateral arch and heel. However the sensors could be distributed in any pattern on the insole according to the practical requirement. For instance, if there is not much variation in the temperature and humidity of heel, then there is no need to dispose the temperature sensor 14 and the humidity sensors 15 around the heel region, instead the entire heel region could be configured to accommodate the pressure sensors 13.

Figure 2:
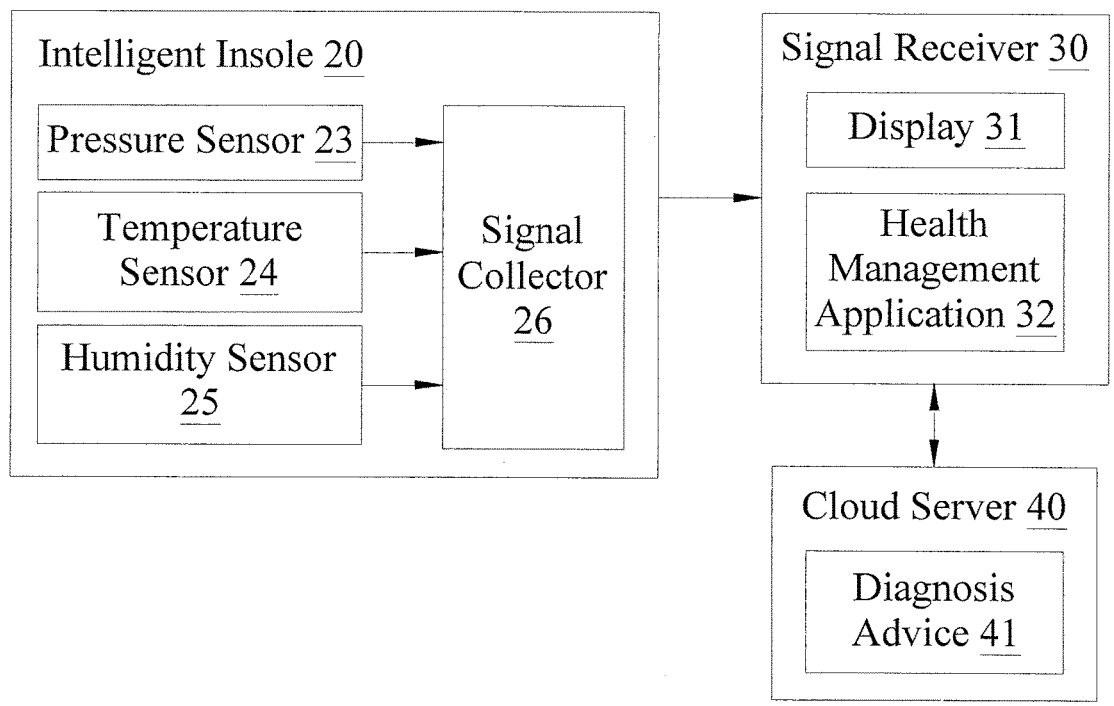
FIG. 2 is the block diagram illustrating the intelligent insole with the health management system of the present invention.

FIG. 2 is the block diagram illustrating the intelligent insole with the health management system of the present invention. As shown in the figure, the intelligent insole may include the pressure sensor 23, the temperature sensor 24 and the humidity sensor 25 configured to collect pressure signal, temperature signal and the humidity signal respectively, then transmit the signals to the signal collector 26. The signal collector 26 could be a transceiver with wireless telecommunication modules such as the Bluetooth, WiFi, RFID, etc. During the 3D printing of the intelligent insole, the pressure sensor 23, the temperature sensor 24 and the humidity sensor 25 could be simultaneously formed on the surface of the intelligent insole. The signal collector 26 may transmit the sensed signals to the signal receiver 30 via wireless communication, wherein the signal receiver 30 could be the handheld mobile devices, e.g. smartphones, tablets or notebooks, the signal receiver 30 connects with the signal collector 26 through the built-in wireless communication module to receive various sensed signals. Meanwhile, a health management application 32 could be installed in the signal receiver 30, which is configured to receive the pressure signal, temperature signal and the humidity signal that will be subsequently converted into actual pressure, temperature and humidity readings, such that the pertaining sensor readings could be presented on the display 31. Therefore, a user is capable of accessing the real-time status of the intelligent insole 20, i.e. the real-time feet status of the user by running the health management application 32 anytime the user desires.

Apart from that, the health management application 32 may set the critical values for each status, for instance the upper limits for the pressure, temperature or the humidity, or the upper limits for the average values of pressure, temperature or the humidity in a scheduled timeframe. For instance, if the received signals show that the average value of feet pressure in a predetermined timeframe exceeds the corresponding critical value, the health management application 32 will issue a warning on the display 31 to remind the user to sit down or relax since the feet are under tension for a prolonged period. If the sensor reading for the temperature exceeds the critical value for the temperature, the health management application 32 will remind the user to switch to slippers for better ventilation. The aforementioned configurations are for the purpose of preventing the health problems due to prolonged walking or tension on feet, or caused by raised temperature and humidity of the feet staying in the shoes for extended period. In addition, since the signal receiver 30 could be a handheld mobile device with wireless communication module, the health management application 32 may connect to the cloud server 40 through the wireless network to upload the readings of pressure, temperature, and the humidity to the cloud server 40 and the readings are stored in the database of the cloud server 40. In addition, the cloud server 40 may be configured to provide the diagnosis advice 41 corresponding to the sensing results. Upon receiving the pressure signal, temperature signal and the humidity signal uploaded by the signal receiver 30, the cloud server 40 is configured to compare the signals with the built-in models to look for the corresponding diagnosis advice 41 which will be transmitted back to the signal receiver 30 and displayed on the display 31. The detailed description of the embodiment will be given hereinafter.

Figure 3:
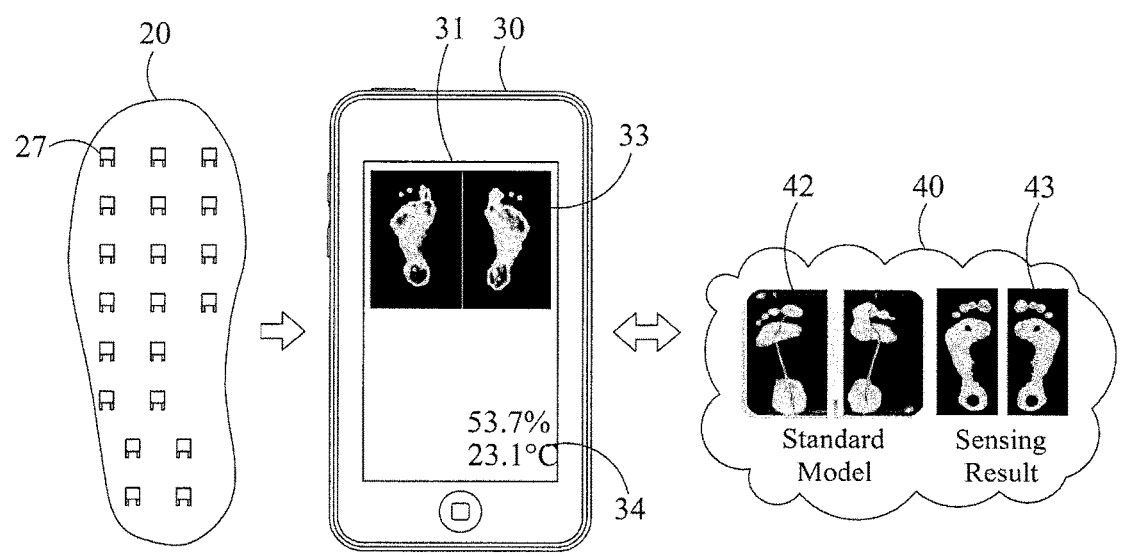
FIG. 3 is the schematic diagram illustrating the intelligent insole with the health management system according to an embodiment of the present invention.

FIG. 3 is the schematic diagram illustrating the intelligent insole with the health management system according to an embodiment of the present invention. As shown in the figure, the intelligent insole 20 includes a plurality of sensors 27, which are simultaneously formed with the insole via 3D printing. Similar to the previous embodiments, the sensors 27 includes the pressure sensor, temperature sensor and the humidity sensor, so redundant details shall be omitted for simplicity. The pressure signal, temperature signal and the humidity signal detected by the sensors 27 will be transmitted to the signal receiver 30 via wireless communication. In the present embodiment, the signal receiver 30 is a smartphone and the health management application 32 is installed in the smartphone; the health management application 32 is configured to convert the sensed signal into actual pressure distribution profile 33 and the temperature and humidity data 34 which will be presented on the display 31 of the smartphone to the user. If the temperature and humidity data 34 exceeds the corresponding critical value, for instance the humidity exceeds 60% or the temperature exceeds 25° C., the signal receiver 30 will notify the user of the warning via the ringing or vibration of the smartphone.

The signal receiver 30 may further upload the pressure distribution profile 33 and the temperature and humidity data 34 to the cloud server 40 in a predetermined time. In addition to storing the sensing result 43, the cloud server 40 is capable of comparing the real-time sensing result 43 and the standard models 42 stored therein in advance, and then transmitting the corresponding diagnosis advice back to the signal receiver 30, such that the user could get the healthcare advice on the feet in real-time. For instance, if the pressure distribution profiles 33 for the left and right foot are inconsistent, the force acting on the feet may be uneven; whereas if pressure in a certain region, e.g. forefoot or heel is too high, the user might be dragging the feet or having unsteady pace. As the result, a healthcare advice is given so that the user could correct his posture. Since there are various types of problems pertaining to foot healthcare, so the types of pressure distribution profiles may be equally abundant too, besides the amount of computing power required to perform the profile comparison might be too much for an ordinary handheld mobile device; therefore, the cloud server 40 is disposed to execute the computations and then transmits the results back to the handheld mobile device for display. For instance, the present invention is capable to point out the central of pressure of the feet from the collected pressure distribution profile, so as to detect the offset of the central of pressure when the user is standing. Ankle inversion or eversion might take place if the central of pressure is deviated to the lateral side or the medial side of the foot, resulting in ankle sprain, the present invention is capable to advice the user to correct the standing posture to avoid such injury. Besides, for the gait of a normal person, most of the pressure on the feet will concentrate in the region around the metatarsus and the heel. However, if the person suffers from foot lesion or has abnormal gait, the pressure will shift to the lateral or medial side of the feet, such as the lateral arch, forming regions with higher pressure which will be represented by different color in an actual embodiment. The health management system is capable of detecting such anomaly in the pressure distribution profile, and then warns the user who is walking that the balance is offset to left or right and causing build-up of excessive pressure at certain region of the feet. If the pressure distribution profile 33 of the feet similar to the one shown in FIG. 3 is collected, the system may propose several advices as follows: 1. The toes of the left and right foot are not used properly, especially the fourth toe and the pinky toe. Such phenomena is due to the ankle eversion, which causes the last two toes to leave the floor and cannot be used as pivots to assist walking, so that the balance for walking is not good. 2. The pressure of the left thumb is slightly higher, so the feet are prone to feet lesions such as the formation of clavus due to single pressure point. Therefore the user is reminded to correct the gait to avoid further damage to the feet.

The descriptions hereinbefore are merely illustrative instead of restrictive. It is understood that various modifications could be applied to the disclosure without deviating from the scope and spirit of the invention that is set forth in the appended claims.

What is claimed is:

1. An intelligent insole, comprising:
   an insole body formed via 3D printing;
   a pressure sensor formed on a surface of the insole body via 3D printing for sensing a pressure signal from the insole body in contact with a foot;
   a temperature sensor formed on the surface of the insole body via 3D printing for sensing a temperature signal of the insole body;
   a humidity sensor formed on the surface of the insole body via 3D printing for sensing a humidity signal of the insole body; and
   a signal transceiver electrically connected to the pressure sensor, the temperature sensor and the humidity sensor to receive the pressure signal, the temperature signal and the humidity signal, respectively, and then transmit the signals to a signal receiver via wireless transmission;
   wherein, the pressure sensor, the temperature sensor, the humidity sensor and the insole body are formed in same 3D printing process, and the pressure sensor, the temperature sensor and the humidity sensor are respectively 0.001 to 0.003 mm in thickness.

2. The intelligent insole of claim 1, wherein the pressure sensor is disposed in a region where the insole body and the foot come into contact, and the pressure sensor measures a variation of electric potential caused by the foot exerting force on the insole body to obtain the pressure signal.

3. The intelligent insole of claim 1, wherein the temperature sensor and the humidity sensor are disposed in a region where the insole body and the foot do not come into contact to sense a temperature and humidity status of the insole and obtain the temperature signal and the humidity signal.

4. The intelligent insole of claim 1, wherein areas of the pressure sensor, the temperature sensor and the humidity sensor are respectively 2 to 8 $mm^2$.

5. The intelligent insole of claim 1, wherein materials for the pressure sensor, the temperature sensor and the humidity sensor comprise electrically conducting metal or piezoelectric material.

6. The intelligent insole of claim 1, wherein the signal receiver is a handheld mobile device displaying sensor readings of the pressure signal, the temperature signal and the humidity signal on a display panel thereof.

7. The intelligent insole of claim 6, wherein the handheld mobile device comprises a health management application comprising a plurality of critical values corresponding to the pressure signal, the temperature signal and the humidity signal, and the health management application sends out a warning when sensed signals exceed the corresponding critical values.

8. The intelligent insole of claim 7, wherein the health management application is configured to connect to a cloud server, upload the pressure signal, the temperature signal and the humidity signal in a predetermined time for storage in the cloud server.

9. The intelligent insole of claim 8, wherein the cloud server comprises a diagnosis advice corresponding to the pressure signal, the temperature signal and the humidity signal, and the diagnosis advice is transmitted back to the handheld mobile device and displayed on the display panel thereof to provide healthcare advices.

* * * * *